United States Patent [19]

Lerner et al.

[11] 4,198,208

[45] Apr. 15, 1980

[54] METHOD AND APPARATUS FOR VAPOR DETECTION

[75] Inventors: Melvin Lerner, Bethesda, Md.; Lyal V. Hood, Annandale, Va.; Marjorie A. Rommel, Westmont, Ill.; Bruce C. Pettitt, Sterling, Va.; Charles M. Erikson, Silver Spring, Md.

[73] Assignee: The United States of America as represented by the Administrator of the National Aeronautics and Space Administration, Washington, D.C.

[21] Appl. No.: 9,885

[22] Filed: Feb. 6, 1979

Related U.S. Application Data

[63] Continuation-in-part of Ser. No. 779,964, Mar. 22, 1977, abandoned.

[51] Int. Cl.² .................. G01N 27/00; G01N 33/00
[52] U.S. Cl. .................... 23/232 R; 23/230 PC; 23/232 E; 422/78; 422/83; 422/98
[58] Field of Search .......... 23/232 R, 232 E, 230 PC; 422/78, 83, 98; 73/23; 260/694

[56] References Cited

U.S. PATENT DOCUMENTS

| | | | |
|---|---|---|---|
| 3,039,053 | 6/1962 | Jacobson | 422/98 |
| 3,374,064 | 3/1968 | Kolsto | 23/232 R |
| 3,460,909 | 8/1969 | Gayle | 23/232 E X |
| 3,711,251 | 1/1973 | Goodson et al. | 23/232 R |
| 3,832,137 | 8/1974 | Mlinko et al. | 23/232 R X |
| 3,877,875 | 4/1975 | Jones et al. | 23/232 R X |
| 3,895,915 | 7/1975 | Haldeman | 422/88 |
| 3,960,495 | 6/1976 | Tantram | 23/232 R X |

*Primary Examiner*—Michael S. Marcus
*Attorney, Agent, or Firm*—Nina M. Lawrence; John R. Manning

[57] ABSTRACT

The method disclosed herein may be practiced by passing the vapors to be sampled along a path with halogen vapor, preferably chlorine vapor, heating the mixed vapors to halogenate those of the sampled vapors subject to halogenation, removing unreacted halogen vapor, and then sensing the vapors for organic halogenated compounds. The apparatus disclosed herein comprises means for flowing the vapors, both sample and halogen vapors, into a common path, means for heating the mixed vapors to effect the halogenation reaction, means for removing unreacted halogen vapor, and a sensing device for sensing halogenated compounds.

By such a method and means, the vapors of low molecular weight hydrocarbons, ketones and alcohols, when present, such as methane, ethane, acetone, ethanol, and the like are converted, at least in part, to halogenated compounds, then the excess halogen removed or trapped, and the resultant vapors of the halogenated compounds sensed or detected. The system is highly sensitive. For example, acetone in a concentration of 30 parts per billion (volume) is readily detected.

15 Claims, 1 Drawing Figure

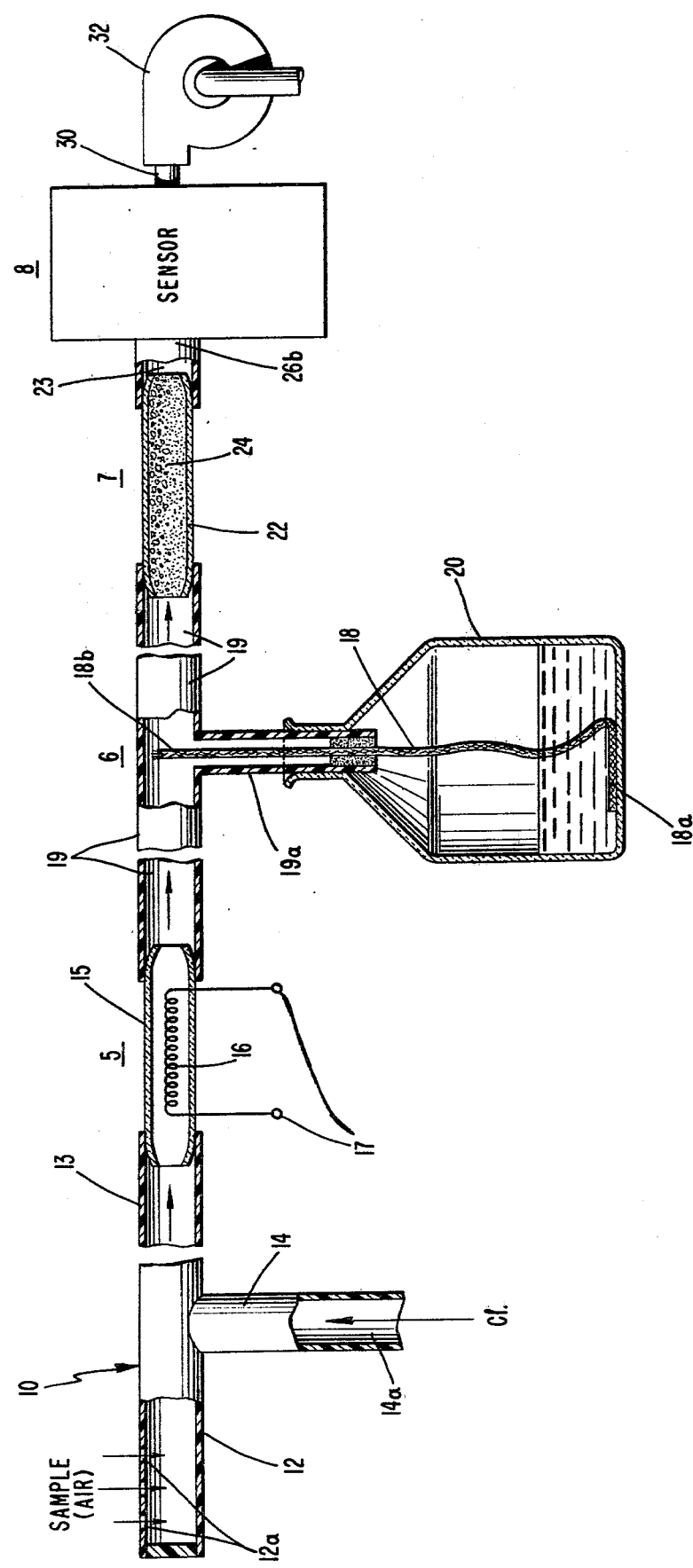

METHOD AND APPARATUS FOR VAPOR DETECTION

ORIGIN OF THE INVENTION

The invention described herein was made by employees of the United States Government and may be manufactured and used by or for the Government for governmental purposes without the payment of any royalties thereon or therefor.

This is a continuation-in-part of our earlier co-pending application Ser. No. 779,964, filed Mar. 22, 1977, and now abandoned.

BACKGROUND OF THE INVENTION

It is known from Rice U.S. Pat. No. 2,550,498 that vapors of various halogen compounds are readily detected in minute quantities in the atmosphere. Sensitivities of one part vapor to a million parts of air (volume basis) are readily achieved. It would be useful to have a detector of similar or even greater sensitivity for the detection of low molecular weight hydrocarbons, ketones and alcohols, such as, for example, methane, ethane, acetone, ethanol and others. Other known vapor or chemical detection methods or systems are found in the following U.S. Pat. Nos.:

3,410,663 to Reilly et al. on Nov. 12, 1968;
3,039,053 to Jacobson on Apr. 10, 1959;
2,550,498 to Rice on Apr. 24, 1951;
3,842,345 to Padgitt et al on Oct. 15, 1974;
3,903,726 to Hirosawa et al on Sept. 9, 1975;
3,725,895 to Haynes on Apr. 3, 1973;
2,283,262 to Kamlet on May 19, 1942;
3,498,309 to Vonderschmitt et al on May 1, 1967;
3,824,079 to Veneme on July 16, 1974;
3,536,088 to Moyat on Oct. 27, 1970;
3,065,411 to Roberts on Nov. 20, 1962;
3,711,251 to Goodson on Jan. 10, 1973.

In the Goodson patent, air containing organic vapor is introduced into a "converter" in which organic vapor, such as organic alcohol, is caused to react with a solid or liquid reactive halogen compound, such as phosphorous pentachloride, contained in the converter. The halogenation reaction produces a halogenated organic compound which is subsequently sensed to detect the presence of organic vapor in the sample undergoing test. It is stated in the Goodson patent that an ethyl alcohol vapor content on the order of 20 gammas per liter of air may be detected. This corresponds to a sensitivity, on a volume basis, of about 9700 parts per billion. Assuming that the same sensitivity of 20 gammas can be achieved with acetone, this corresponds to a sensitivity, on a volume basis, of about 7700 parts per billion. While this sensitivity is good, even greater sensitivity is highly desirable.

SUMMARY OF THE INVENTION

In accordance with the present invention, applicants have provided a very sensitive method and apparatus for detecting organic vapors. The method and apparatus are much more sensitive, by far, than the Goodson system which, as mentioned above, has a good sensitivity on the order of about 1 part per million. In accordance with the present invention, applicants provide a system for detection of organic vapor which is over two hundred times more sensitive than the sensitivity reported by Goodson. For example, applicants can detect acetone in an amount of 30 parts per billion, which is about 260 times more sensitive than the value of 20 gammas per liter reported by Goodson.

These results are achieved in accordance with the present invention by mixing a sample vapor comprising the vapor of an organic compound susceptible of halogenation and the vapor of chlorine and/or bromine, heating the mixed vapors in a reaction zone at a temperature of from 825° to 925° C. for a time sufficient to effect halogenation of the organic compound to form a halogenated organic compound, removing unreacted halogen vapor from the mixed vapors, and thereafter sensing the halogenated organic compound to detect the presence of the organic compound in the sample vapor. Apparatus for carrying out the method includes means for creating a vapor flow, means for inserting into the flow path a mixture of the sample vapor and the chlorine and/or bromine vapor, means for heating the mixture in the flow to effect halogenation of the organic compound, means for removal of unreacted halogen, and means for sensing the halogenated organic compound to detect the presence of the organic compound in the sample vapor.

The sensing means used in the invention can be any suitable known device such as that disclosed in the Goodson patent. Further details concerning these known sensing devices are given in the prior art such as in the Rice U.S. Pat. No. 2,550,498 and in the Roberts U.S. Pat. No. 3,065,411, mentioned above.

The remarkable increase in sensitivity achieved in the present invention is quite unexpected and is believed to be due to the high temperature, vapor phase halogenation reaction. As mentioned above, halogenation is effected with halogen vapor in a reaction zone at a temperature of about from 825° to 925° C. In our parent application, a temperature range of 825° to 900° C. is disclosed and that range is suitable as is a range of 850° to 925° C. In general, the temperature is chosen to achieve optimum chlorination efficiency. At the temperatures employed in the present invention, the reaction is extremely efficient in introducing chlorine into the reaction products. Under optimal temperature conditions, thermal cracking and chlorination of the organic compound occur and excess chlorine vapor is used to promote the formation of multichlorinated reaction products such as chloroform and carbon tetrachloride. A thermionic sensor, such as that of the Rice or Roberts patents mentioned above, is responsive to the number of halogen atoms incorporated in the molecule. Accordingly, sensitivity is enhanced where the reaction products are multichlorinated. In addition, the gas phase chlorination of the present invention facilitates control of the chlorination reagent (chlorine gas) to maintain a constant excess chlorine concentration which assures a high level of performance of the detector. While an excess of halogen gas is used, it is preferred not to use an excessive quantity in order to more readily remove unreacted halogen from the system and thus reduce the "noise" of the system. For example, when the organic compound to be detected is present in an amount measured in parts per billion, it is preferred to use chlorine in an amount measured in parts per million. Since the chlorine gas is supplied to the reaction, there is no significant depletion or change in the chlorination reagent such as would occur where a fixed amount of solid or liquid chlorination reagent is employed such as in the Goodson patent mentioned above.

Since an excess of chlorine is used, it is important to remove unreacted chlorine from the system and the preferred system is to pass the mixed gases, after effecting the high temperature chlorination reaction, in contact with a plurality of copper particles, e.g. having a particle size of 40–100 mesh.

BRIEF DESCRIPTION OF THE DRAWINGS

The sole FIGURE of the drawings is a diagrammatic representation of an apparatus embodying the invention and suitable for practicing the method thereof.

DESCRIPTION OF PREFERRED EMBODIMENTS

Referring to the sole FIGURE, a flexible Teflon tubing 10 has two branches 12 and 14. The orifices or opening 12 of the branch 12 are placed or passed adjacent to the vapor or the material the vapor from which is to be sampled, the orifice or opening 14a of the branch 14 is arranged to receive halogen vapor, (chlorine and/or bromine), from a suitable source indicated by the chemical symbol for chlorine. Air and any vapor of the organic compound in question is admitted through orifices 12a. The vapors flow through the tubings 12 and 14, which may be No. 20 Teflon tubing, in the direction of the arrows and mix in the tubing 13, continuing in the direction of the arrow shown in the diagram.

A heater 5 comprises platinum wire 16 arranged in the flow from the tubing 14. It may be in a coil as shown or it may be a simple section of wire transversely or longitudinally arranged in the tubing 13. In a successful embodiment, the platinum heater wire is housed in a pyrex glass tube or reactor 15 about 15 cm. long and 5 mm. i.d. This glass tube is fitted with adapters for connection to the No. 20 Teflon tubing 13 from the chlorine source and sampling probe, and to a like tubing 19 leading from the glass tube 15. The wire 16 is connected from its terminals 17 to a suitable source of heating voltage, indicated as a d.c. (direct current) source, but may equally well be connected to a suitable a.c. (alternating current) source. The voltage is regulated so as to heat the mixed gases to a temperature to effect chlorination of the organic compound in reactor 5.

Optional humidifier 6 comprises a wick 18, which may be similar to the wick conventionally used in a kerosene lantern trimmed smaller, or it may be a suitable piece of cotton cloth. One end 18a of wick 18 is immersed in a reservoir 20 of water. In the illustrated embodiment, the polyethylene tubing 19 includes a branch 19a. The open end of branch 19a is squeezed into the neck of reservoir or container 20, so that little or no air is drawn through branch 19a into the vapor flow. The reservoir 20 contains water into which one end 18a of the wick 18 is dipped. The other end 18b of the wick is frayed to facilitate entry of water vapor into the main stream of the vapor flow. The exact penetration of the wick into the vapor flow path may be adjusted depending on ambient humidity conditions for best operation. The wick creates an atmosphere of humidity in its immediate vicinity and humidifies the vapors drawn downstream from the wire 16. Other humidifying means may be employed.

Next downstream is a trap 7 for the unreacted chlorine and/or bromine, and comprises a container 22 which receives at its inlet the downstream end of tube 19 and which is closed and substantially air-tight. The downstream end of tubing 19 is sealed in air-tight or near air-tight manner to the container 22. The container 22 contains material to react with and trap the free chlorine; for example, it may be filled with finely divided potassium hydroxide on floisil, or, what is deemed preferably, finely divided copper 24. The container 22 may be a pyrex glass tube 15 cm. long, and 5 mm. i.d., such as housed the platinum heating wire 16, with similar fittings. A further tubing 23 has one upstream end sealed in air-tight or nearly air-tight manner to the downstream end of container 24. The other end of the tubing 23 leads to a sensor 8. A further tubing 30 leads from the sensor 8 to a pump 32 which induces the vapor flow through the system from left to right in the sense of the drawing.

In operation of this apparatus, the part of tubing 12 with the openings 12a may be part of a wand or probe placed near or passed along an area from which the vapors of the organic compound to be detected may be found. By way of example, the tubings 12, 13, 14, 19, 23, and 30 may be of small internal diameter, for example, about 3 mm. or less, such as the No. 20 Teflon tubing mentioned above. The purpose of employing a small internal diameter conduit for passage of the vapors is to reduce the volume to be drawn by pump 32 so that with a modest pump force, the vapors will pass quickly through the system and a test may thus be performed in a short time. The pump 32 may be a diaphragm pump which draws, for example, about 500 c.c. of air per minute. The total length of tubings may be about five meters and the total volume in the tubing and container 22 may be only above five c.c., so that the sample, after passing through the tubing 13, catalyst 5, vaporizer 6, and trap 7, may arrive at the sensor 8 in approximately a second or less from the beginning of the test.

The source of chlorine vapor may be a cylinder of chlorine gas or it may be generated electrochemically from a nickel chloride solution in known manner. It may be made available, activated or operated only when tests are being conducted.

The mixed vapors of chlorine, air, and sample travel the path through tubing 10 and are exposed to the heater wire 16. The wire 16 is preferably heated such that the temperature of the mixed gases is raised to about 825° to 925° C. The temperature of the heater wire may be stabilized, if desired, by connecting the wire 16 via terminals 17 as one arm of a wheatstone bridge. The resistance of the wire 16 will vary with temperature, unbalancing the bridge when the wire becomes either warmer or cooler than the balancing temperature and therefore increasing or decreasing the resistance of the wire from that which balances the bridge. Whichever way the bridge is unbalanced results in a decrease or increase of current through the wire 16 to increase or decrease the resistance of the wire and restore the balance of the bridge. Circuits to accomplish the desired constancy of wire temperature and resistance are known.

The sensor may comprise an arrangement such as described in the Rice U.S. Pat. No. 2,550,498 or the Roberts U.S. Pat. No. 3,065,411 mentioned above. Suitable sensors for thus detecting halogenated vapors are sold commercially by General Electric, the assignee of the Rice and Roberts patents. Alternatively, one may use an electron capture detector. We have successfully used an electron capture detector sold commercially by Analog Technology Corporation and sold as "Wide Dynamic Range Electron Capture Detector." It is well, in operation, to permit some five minutes or so as startup time prior to operation to allow the circuits to stabilize and the desired heater wire temperature to be reached. All the circuits are desirably solid state, either transistorized or employing integrated circuits or the like.

As a result of exposure to the high temperature chlorination reaction conditions existing in reactor 5, if any low molecular weight organic compounds, such as hydrocarbons, ketones or alcohols exist in the mixture of gases, some at least will react with the chlorine vapor and are converted into halogen compounds of the kind referred to in the Rice patent mentioned above.

It is now desirable to remove excess chlorine in the mixture lest the free chlorine give a false indication in the sensor. For this purpose, the vapors are passed from the tubing 10 through the trap 7, preferably comprising copper powder 24. The powder should not be so fine as to obstruct or occlude the flow of gas under the influence of the pressure used, nor so coarse that the gases flowing through the powder will fail to come into close reactive contact with the copper particles. For this purpose, in the present example, copper powder from a commercial source of nominal fineness 40 to 100 mesh (mesh indicates the number of openings per linear inch through which the material will pass) is passed through a sieve of about 80 mesh to remove fines. The resultant copper powder of about 40 to 80 mesh retained on the screen provides the desired particle size.

Moreover, we have found that the reaction of the fine chlorine with the copper is facilitated by the presence of a certain amount of water vapor or humidity in the vapor flow through the copper powder 24 by the humidifier 6. In fact, when the air has sufficient humidity (generally about 25% or more relative humidity), we have found that we may dispense with the wick 18. Nevertheless, to assure consistent and uniform operation, the wick 18, consisting of a simple strip of cotton cloth having a portion immersed in the water in container 20 is preferred. By surface tension, the wick absorbs water and exposes the flow of vapors through tubing 10 sufficiently to enhance the humidity, if otherwise insufficient, of the vapors as they progress in their path to and through the powder 24 of the trap 7. It is apparent that other suitable humidifying means may be used, the wick being, however, especially simple and well suited to the purpose. The humidity may be introduced at any point in the path prior to the halogen trap.

The vapors pass through the trap 7 comprising the copper powder 24 which traps substantially all the free chlorine which combines with the copper, and the vapors absent the free chlorine continue their path through tubing 23 to the sensor 8.

It has been experimentally determined that by the apparatus and method described above, the vapors of low molecular weight hydrocarbons, ketones and alcohols may be detected in astonishingly small amounts, for example, less than one part per million and as low as thirty parts per billion, of vapors such as acetone or ethanol. Thus, there has been disclosed a method and apparatus highly sensitive and especially useful for detecting the presence (or absence) from the atmosphere of vapors of low molecular weight of hydrocarbons, ketones and alcohols such as ethane, methane, acetone, or ethanol.

In our parent application Ser. No. 779,964, we expressed the theory that catalysis was necessary to effect the chlorination reaction. We have now discovered that catalysis is not essential. As shown in the data which follows, the system achieves full sensitivity at high temperature in the absence of a catalyst. The system employed in making the comparison is as described above in connection with the drawing except that the reactor 5 comprises a plain quartz tube, externally heated, with no platinum or other catalytic material present. The data obtained from several runs is listed in Table I below. A sensitivity of as low as thirty parts per billion is readily achieved.

TABLE 1

| Run No. | Acetone Concentration in Sample Air (parts per billion) (By volume) | Detector Output (Volts) |
| --- | --- | --- |
| 1 | 29 | .462 |
| 2 | 58 | .467 |
| 3 | 86 | .469 |
| 4 | 115 | .476 |
| 5 | 144 | .483 |
| 6 | 413 | .487 |
| 7 | 825 | .543 |
| 8 | 1238 | .607 |
| 9 | 1625 | .651 |
| 10 | 2000 | .662 |

Acetone concentrations are obtained from a calibrated leak source. The response is linear (correlation coefficient=0.98) over the range of 25 to 2000 parts per billion investigated. The concentration of 30 parts per billion represents a practical detection level obtained in operating environments. Even greater sensitivity is available under more controlled conditions such as exist in the laboratory. Unreacted chlorine, of course, is also detected and, as such, represents "noise" in the system. Using the copper trap mentioned above, the noise level is quite low. For example, using the system described above, the ratio of sensor output when chlorine is flowing relative to the sensor output when the chlorine is not flowing, is 1.39. The signal to noise (rms noise) in the range of 100 to 30 ppb gives a signal to noise ratio of 8 at 100 ppb, 3.4 at 50 ppb and 1.5 at 30 ppb.

In the foregoing specification, sensitivity values are given in parts by volume.

What is claimed is:

1. A method for detecting vapors of an organic compound at elevated temperature to form a halogenated organic compound susceptible of halogenation comprising the steps of mixing a sample vapor comprising vapor of an organic compound susceptible of halogenation and vapor of a halogen selected from the group consisting of chlorine and bromine, maintaining the mixed vapors in a reaction zone at a temperature of from 825° to 925° C. for a time sufficient to effect halogenation of said organic compound to form a halogenated organic compound, removing unreacted halogen vapor from said mixed vapors, and thereafter sensing the halogenated organic compound to detect the presence of said organic compound in the sample vapor.

2. A method according to claim 1 wherein said temperature is from 825°–900° C.

3. A method according to claim 1 wherein said temperature is from 850° to 925° C.

4. A method according to claim 1 wherein said halogen vapor comprises chlorine.

5. A method according to claim 1 wherein said organic compound comprises acetone.

6. A method according to claim 1 wherein the unreacted halogen vapor is removed from the mixture of vapors by contacting the mixture of vapors with copper.

7. A method according to claim 1 further including the step of humidifying the vapors prior to removing the unreacted halogen vapor therefrom.

8. A method according to claim 7 wherein the vapors are humidified after effecting halogenation of said organic compound.

9. A method according to claim 1 wherein the mixed vapors are heated in the presence of a catalyst for the halogenation of the organic compound.

10. A method according to claim 9 wherein said catalyst comprises platinum.

11. Apparatus for detecting organic vapors of an organic compound susceptible of halogenation at elevated temperature to form a halogenated organic compound comprising means for creating a vapor flow, means for inserting into the flow path a mixture of a sample vapor comprising vapor of an organic compound susceptible of halogenation and vapor of a halogen selected from the group consisting of chlorine and bromine, means for thermally cracking the organic compound in said flow to effect halogenation of the organic compound, means for removal of unreacted halogen vapor, and means in said flow downstream of the halogen vapor removal means for sensing the halogenated organic compound to detect the presence of said organic compound in the sample vapor.

12. Apparatus according to claim 11 wherein said halogen vapor removal means comprises a plurality of copper particles located in said flow path.

13. Apparatus according to claim 11 further including catalyst means in said flowpath for catalyzing the halogenation of said organic compound.

14. Apparatus according to claim 11 further including means for humidifying the vapor in said flowpath upstream of said unreacted halogen vapor removal means.

15. Apparatus according to claim 14 wherein said humidifying means is located downstream of said heating means.

* * * * *

UNITED STATES PATENT OFFICE
CERTIFICATE OF CORRECTION

PATENT NO. : 4,198,208

DATED : April 15, 1980

INVENTOR(S) : Melvin Lerner, Lyal V. Hood, Marjorie A. Rommell, Bruce C. Pettitt and Charles M. Erikson It is certified that error appears in the above-identified patent and that said Letters Patent are hereby corrected as shown below:

On the introductory page, item [73] in column one:

Delete "The United States of America as Represented by the Administrator of the National Aeronautics and Space Administration, Washington, D.C."

and

Insert --The United States of America as Represented by the Secretary of the Treasury, Washington, D. C. --.

Signed and Sealed this

Twelfth Day of August 1980

[SEAL]

*Attest:*

SIDNEY A. DIAMOND

*Attesting Officer*  *Commissioner of Patents and Trademarks*